United States Patent
Higashi et al.

(10) Patent No.: US 10,226,441 B2
(45) Date of Patent: Mar. 12, 2019

(54) AGING INHIBITOR

(71) Applicant: NIHON SIZEN HAKKOH CO., LTD., Takayama-shi (JP)

(72) Inventors: Naoki Higashi, Ota-ku (JP); Masahiro Nakanishi, Takayama (JP)

(73) Assignee: NIHON SIZEN HAKKOH CO., LTD., Takayama-shi (JP)

( * ) Notice: Subject to any disclaimer, the term of this patent is extended or adjusted under 35 U.S.C. 154(b) by 0 days.

(21) Appl. No.: 15/534,319

(22) PCT Filed: Dec. 1, 2015

(86) PCT No.: PCT/JP2015/083686
§ 371 (c)(1),
(2) Date: Jun. 8, 2017

(87) PCT Pub. No.: WO2016/093104
PCT Pub. Date: Jun. 16, 2016

(65) Prior Publication Data
US 2017/0360733 A1    Dec. 21, 2017

(30) Foreign Application Priority Data
Dec. 9, 2014  (JP) .................... 2014-248884

(51) Int. Cl.
*A61K 31/198*    (2006.01)
*A23K 10/12*    (2016.01)
(Continued)

(52) U.S. Cl.
CPC ............ *A61K 31/198* (2013.01); *A23K 10/12* (2016.05); *A23K 50/50* (2016.05); *A23L 2/52* (2013.01); *A23L 33/105* (2016.08); *A61K 8/99* (2013.01); *A61K 31/19* (2013.01); *A61K 31/192* (2013.01); *A61K 31/194* (2013.01); *A61K 31/196* (2013.01); *A61K 31/197* (2013.01); *A61K 31/352* (2013.01); *A61K 31/353* (2013.01);
(Continued)

(58) Field of Classification Search
None
See application file for complete search history.

(56) References Cited

U.S. PATENT DOCUMENTS

2003/0161910 A1    8/2003    Aoki et al.
2015/0306158 A1    10/2015    Kim et al.

FOREIGN PATENT DOCUMENTS

CN    101536763 A    9/2009
JP    09-294560 A    11/1997
(Continued)

OTHER PUBLICATIONS

Written Opinion of the International Searching Authority for PCT/JP2015/083686 , English Translation. (Year: 2015).*
English Abstract: Okada, et al., J. Jpn. Soc. Nutr. Food Sci., 58:209. (Year: 2005).*
Okada, H. et al., "Structural Analysis and Synthesis of Oligosaccharides Isolated from Fermented Beverage of Plant Extract", Japanese Society of Applied Glycoscience, 2008, vol. 55, No. 2, pp. 143-148.
Okada, H. et al, "Antioxidative Activity and Protective Effect of Fermented Plant Extract on Ethanol-induced Damage to Rat Gastric Mucosa", J. Japan Soc. Nutr. Food Science, 2005, vol. 58, pp. 209-215 (w/ English Summary of article).
(Continued)

*Primary Examiner* — Michael Barker
(74) *Attorney, Agent, or Firm* — Oblon, McClelland, Maier & Neustadt, L.L.P.

(57) ABSTRACT

An object of the present invention is to provide a senescence retarding agent that delays the onset of senescence symptoms and extends longevity, and is superior in safety. The senescence retarding agent of the present invention that achieves the object is characterized by containing a plant fermentation product as an active ingredient, the plant fermentation product being a mixture of the following: (a) a koji mold-fermented product of one or more kinds of beans and/or cereals selected from the group consisting of barley, black soybean, red rice, black rice, adzuki bean, adlay, Japanese millet, foxtail millet, and millet; (b) a yeast- and/or lactic acid bacterium-fermented product of one or more kinds of fruits selected from the group consisting of mikan (mandarin orange), grape, apple, yama-budo (crimson glory grape), peach, kaki (Japanese persimmon), *papaya*, nashi (Japanese pear), watermelon, ume (Japanese apricot), fig, karin (Chinese quince), pumpkin, kumquat, yuzu (Chinese lemon), loquat, apricot, jujube, chestnut, matatabi (silvervine), and sumomo (Japanese plum); (c) a yeast- and/or lactic acid bacterium-fermented product of one or more kinds of root crops and/or potatoes selected from the group consisting of murasaki-imo (purple sweet potato), kikuimo (Jerusalem artichoke), carrot, onion, satsuma-imo (sweet potato), satoimo (taro), jinenzyo (Japanese yam), daikon (Japanese radish), akakabu (red turnip), gobo (burdock root), renkon (lotus root), yacon, yuri-ne (lily bulb), kuwai (arrowhead), ginger, garlic, and turmeric; (d) a yeast- and/or lactic acid bacterium-fermented product of one or more kinds of flowers and/or leaf vegetables selected from the group consisting of cabbage, shiso (*perilla*), mulberry leaves, dokudami (Korean houttuynia), yomogi (wormwood), kumazasa (kuma bamboo grass), and dandelion; (e) a yeast- and/or lactic acid bacterium-fermented product of one or more kinds of seaweeds selected from the group consisting of kombu (sea tangle), wakame (*Undaria pinnatifida*), and mozuku (*Nemacystus decipiens*); (f) a yeast- and/or lactic acid bacterium-fermented product of one or more kinds of seeds selected from the group consisting of black sesame seeds, walnuts, and ginkgo nuts; and (g) a yeast- and/or lactic acid bacterium-fermented product of one or two kinds of mushrooms selected from the group consisting of maitake (*Grifola frondosa*) and shiitake (*Lentinus edodes*).

9 Claims, 6 Drawing Sheets

(51) Int. Cl.

| | | |
|---|---|---|
| *A23L 33/105* | (2016.01) | |
| *A61K 8/99* | (2017.01) | |
| *A61K 35/744* | (2015.01) | |
| *A61K 36/03* | (2006.01) | |
| *A61K 36/062* | (2006.01) | |
| *A61K 36/064* | (2006.01) | |
| *A61K 36/07* | (2006.01) | |
| *A61K 36/16* | (2006.01) | |
| *A61K 36/185* | (2006.01) | |
| *A61K 36/23* | (2006.01) | |
| *A61K 36/28* | (2006.01) | |
| *A61K 36/282* | (2006.01) | |
| *A61K 36/31* | (2006.01) | |
| *A61K 36/39* | (2006.01) | |
| *A61K 36/42* | (2006.01) | |
| *A61K 36/44* | (2006.01) | |
| *A61K 36/48* | (2006.01) | |
| *A61K 36/49* | (2006.01) | |
| *A61K 36/52* | (2006.01) | |
| *A61K 36/75* | (2006.01) | |
| *A61K 36/899* | (2006.01) | |
| *A61K 31/19* | (2006.01) | |
| *A61K 31/192* | (2006.01) | |
| *A61K 31/194* | (2006.01) | |
| *A61K 31/196* | (2006.01) | |
| *A61K 31/197* | (2006.01) | |
| *A61K 31/352* | (2006.01) | |
| *A61K 31/353* | (2006.01) | |
| *A61K 31/401* | (2006.01) | |
| *A61K 31/405* | (2006.01) | |
| *A61K 31/4172* | (2006.01) | |
| *A23K 50/50* | (2016.01) | |
| *A23L 2/52* | (2006.01) | |
| *A61K 36/535* | (2006.01) | |
| *A61K 36/60* | (2006.01) | |
| *A61K 36/605* | (2006.01) | |
| *A61K 36/73* | (2006.01) | |
| *A61K 36/736* | (2006.01) | |
| *A61K 36/752* | (2006.01) | |
| *A61K 36/78* | (2006.01) | |
| *A61K 36/81* | (2006.01) | |
| *A61K 36/87* | (2006.01) | |
| *A61K 36/88* | (2006.01) | |
| *A61K 36/888* | (2006.01) | |
| *A61K 36/8945* | (2006.01) | |
| *A61K 36/8962* | (2006.01) | |
| *A61K 36/8967* | (2006.01) | |
| *A61K 36/8994* | (2006.01) | |
| *A61K 36/8998* | (2006.01) | |
| *A61K 36/9066* | (2006.01) | |
| *A61K 36/9068* | (2006.01) | |

(52) U.S. Cl.
CPC .......... *A61K 31/401* (2013.01); *A61K 31/405* (2013.01); *A61K 31/4172* (2013.01); *A61K 35/744* (2013.01); *A61K 36/03* (2013.01); *A61K 36/062* (2013.01); *A61K 36/064* (2013.01); *A61K 36/07* (2013.01); *A61K 36/16* (2013.01); *A61K 36/185* (2013.01); *A61K 36/23* (2013.01); *A61K 36/28* (2013.01); *A61K 36/282* (2013.01); *A61K 36/31* (2013.01); *A61K 36/39* (2013.01); *A61K 36/42* (2013.01); *A61K 36/44* (2013.01); *A61K 36/48* (2013.01); *A61K 36/49* (2013.01); *A61K 36/52* (2013.01); *A61K 36/535* (2013.01); *A61K 36/60* (2013.01); *A61K 36/605* (2013.01); *A61K 36/73* (2013.01); *A61K 36/736* (2013.01); *A61K 36/75* (2013.01); *A61K 36/752* (2013.01); *A61K 36/78* (2013.01); *A61K 36/81* (2013.01); *A61K 36/87* (2013.01); *A61K 36/88* (2013.01); *A61K 36/888* (2013.01); *A61K 36/899* (2013.01); *A61K 36/8945* (2013.01); *A61K 36/8962* (2013.01); *A61K 36/8967* (2013.01); *A61K 36/8994* (2013.01); *A61K 36/8998* (2013.01); *A61K 36/9066* (2013.01); *A61K 36/9068* (2013.01); *A23V 2002/00* (2013.01)

(56) References Cited

FOREIGN PATENT DOCUMENTS

| | | |
|---|---|---|
| JP | 2001-333751 A | 12/2001 |
| JP | 2003-061612 A | 3/2003 |
| JP | 2004-173692 A | 6/2004 |
| JP | 2005-110560 A | 4/2005 |
| JP | 2006-515590 A | 6/2006 |
| JP | 2007-145809 A | 6/2007 |
| JP | 2007-167017 A | 7/2007 |
| JP | 2007-175064 A | 7/2007 |
| JP | 2008-94795 A | 4/2008 |
| JP | 2008-120726 A | 5/2008 |
| JP | 2008-231002 A | 10/2008 |
| JP | 2010-30958 A | 2/2010 |
| JP | 2010-208969 A | 9/2010 |
| JP | 2010-270012 A | 12/2010 |
| JP | 2011-142904 A | 7/2011 |
| JP | 2011-213660 A | 10/2011 |
| JP | 2012-207004 A | 10/2012 |
| JP | 2012-246242 A | 12/2012 |
| JP | 2013-249260 A | 12/2013 |
| JP | 2014-003929 A | 1/2014 |
| JP | 2014-187997 A | 10/2014 |
| JP | 2015-526085 A | 9/2015 |
| WO | 2001/093696 A1 | 12/2001 |
| WO | 2004/058213 A1 | 7/2004 |
| WO | 2007/102572 A1 | 9/2007 |
| WO | 2014/027864 A1 | 2/2014 |

OTHER PUBLICATIONS

Dillin, A. et al., "Rate of Behavior and Aging Specified by Mitochondrial Function During Development", Science Magazine, Dec. 2002, vol. 298, pp. 2398-2401.

Grandison, R. et al., "Amino-acid imbalance explains extension of lifespan by dietary restriction in *Drosophila*", Nature, Dec. 2009, vol. 462, pp. 1061-1064.

Ide, T., "Understanding Studies on Aging", Yodosha Co., Ltd., 2002, pp. 20-28.

Coleman, R.J. et al., "Caloric Restriction Delays Disease Onset and Mortality in Rhesus Monkeys", Science Magazine, Jul. 2009, vol. 325, pp. 201-204.

Chiba, T. et al., "Calorie Restriction Mimetics", Experimental Medicine, 2013, vol. 31, No. 20, pp. 182-189.

Ueki, K., "Insulin and IGF-1 signals and control of aging and longevity", Experimental Medicine, 2013, vol. 31, No. 20, pp. 22-27.

Baur, J. et al., "Resveratrol improves health and survival of mice on a high-calorie diet", Nature, 2006, vol. 444, No. 7117, pp. 337-342 [pp. 1-16].

Yagi, Y. et al., "Effect of a Red Wine-derived Polyphenol Protocatechuic Acid on the Lifespan of *Drosophila Melanogaster*", Food Function, 2013, vol. 11, pp. 9-13 (w/ English abstract).

Sinclair, D.A. et al., "Small Molecule Modulators of Sirtuins", Experimental Medicine, 2013, vol. 31, No. 20, pp. 209-217.

Imai, S. et al., "Science of aging and longevity", Experimental Medicine, 2013, vol. 31, No. 20.

(56) References Cited

OTHER PUBLICATIONS

Hoeijmakers, J., "Genome Maintenance Mechanisms for Preventing Cancer", Nature, 2001, vol. 411, pp. 366-374.

Ito, A., "Benefits of Miso Removing Radioactive Substances—a Physiological Effect by Miso of Preventing Cancer", Forefront of Miso Science, Japan Miso Promotion Board,1999, pp. 1-5.

Ashida et al., "The Defensive Effects of a Fermented Vegetable Product on X-ray Exposure—Effects on the Regeneration of Intestinal Crypts", The Journal of Japan Mibyou System, 2006, vol. 12, No. 1, pp. 129-131.

Yan, J. et al., "Reduced Coenzyme Q10 Supplementation Decelerates Senescence in SAMP1 Mice", Experimental Gerontology, 2006, vol. 41, pp. 130-140.

Kohno, A. et al., "Effect of chronic feeding of soy protein isolate on the advance of senescence in the senescence accelerated mouse (SAM)", Nutr. Sci. Soy Protein, Jpn. 7, 1986, pp. 25-29 (w/ English abstract).

Yanase, S. et al., "Analysis of Aging", Nematodes Labo Manual, Springer-Verlag Tokyo, Inc., 2003, pp. 201-206.

Combined Office Action and Search Report dated Dec. 22, 2017 in Chinese Patent Application No. 201580067409.8 (with English translation of categories of cited documents) citing document AO therein, 8 pages.

\* cited by examiner

AGING INHIBITOR

TECHNICAL FIELD

The present invention relates to a senescence retarding agent employing a plant fermentation product. Particularly, the present invention relates to a senescence retarding agent that has an action of retarding the onset of senescence symptoms associated with aging of animals and an action of prolonging their survival and is superior in safety.

BACKGROUND ART

Senescence is an unavoidable phenomenon for animals. Progress in life science leads to advances in studies on senescence, revealing senescence events at the levels of an individual and of organs, tissues, cells, and genes, and in addition, cooperative working of nerves and vessels, immune regulation, and substances of various types, such as hormones and regulatory factors, that provide their linkage, and yet the detailed mechanism of senescence has not become revealed. However, there have been found clues for elucidating the mechanism of senescence, and it has become widely known that in animals, such as nematodes, fruit flies, rats, mice, and monkeys, dietary caloric restriction provides an effect of extending their longevity (Non-Patent Literatures 1 to 4). It is estimated that the energy metabolism in mitochondria is involved in this context. In addition, calorie restriction mimetics have also been sought with the view of retarding senescence and extending longevity (Non-Patent Literature 5). The relation between insulin and growth factor (IGF-1) signals and longevity has also been found as a common signaling pathway in nematodes, fruit flies, and mammals (mice) (Non-Patent Literature 6). Further, there have been found results that resveratrol, a low molecular weight component contained in red grapes, is expected to have an action of retarding senescence and an effect of extending longevity (Non-Patent Literature 7), and investigations are being carried out to seek for analogous substances (Non-Patent Literature 8). Recently, sirtuins have been found to have an enzymatic activity of deacetylation of histones and to be involved in extending longevity, and are expected to be associated with senescence as clues for further studies. Small molecule modulators of sirtuins have also been found (Non-Patent Literature 9).

It would be difficult to stop senescence symptoms that occur with aging, but one wants to retard the onset of senescence symptoms and in addition, to extend his/her longevity. However, it is estimated that more than one gene and process are responsible for the cause of these senescence symptoms (Non-Patent Literature 10). For this reason, testing using animal individuals is required for evaluation of the delay of the onset of senescence symptoms or the prolongation of longevity. In addition, model animals with a short generation time are necessary for examination and investigation on longevity. Such model animals include nematodes, fruit flies, and mice. Among these, mice are mammalian and have a longevity of about two to three years even in the case of normal mice, and therefore, can be used to estimate effects on senescence and longevity in a relatively short period of time. Mice of the SAM-P line, which is a senescence accelerated model mouse line that was found in mice of the AKR line at an animal experiment facility at Kyoto University, have a longevity of about 1.5 years and display various symptoms characteristic of senescence, and thus are used widely in studying senescence in comparison with SAM-R1 mice, which are of a normal type of the same line. Mice of these types have been passaged and propagated by and are commercially available from the Council for SAM Research, and methods for evaluating senescence symptoms have also been standardized by the Council for SAM Research. As the standardized senescence indexes, use is made of abnormal or slow behavior, eye symptoms (periocular erosion, cloudycornea, cataract, and the like), hair loss, senescence symptoms of the skin, such as the coat of hair, and backbone curvature. On the other hand, the prolongation of survival, which is an index of retarded senescence, is not included in the standard evaluation indexes defined by the Council for SAM Research.

Symptoms similar to those in the case of senescence have also been observed in damage caused by irradiation of radiation (Non-Patent Literature 11). It has been reported by Ito et al. that damage was caused in mucosal stem cells of the small intestine of mice which had been irradiated with 6 to 14 grays of X-ray radiation, while mice which had received miso (a Japanese fermented soybean paste) in combination with feed had less damage of stem cells of crypts of the small intestine (Non-Patent Literature 12). However, Ito et al. has not given any report on senescence symptoms or the survival rate of mice. It has been reported that using a similar evaluation system, Manda Koso, which is a plant fermentation food, was effective in the prevention of damage of mucosal stem cells of the small intestine of X-ray irradiated mice (Non-Patent Literature 13), but there was no report on the retardation of senescence symptoms or prolongation of the survival of mice by Manda Koso.

Furthermore, it has been reported that in cases where senescence accelerated model mice of the SAM-P1 line were employed, coenzyme Q10 and its reduced form exerted an effect of preventing senescence symptoms (Non-Patent Literature 14). In comparison with mice without added CoQ10, mice receiving CoQ10 exhibited a significant effect of preventing senescence in terms of eye symptoms, skin symptoms, backbone curvature, and total symptom score, and yet, did not have an extended longevity. It has also been reported that when effects of soybean proteins SPI and casein on senescence were compared, there was observed no difference in the degree of senescence between for both proteins, while SPI was found to have a survival prolonging effect (Non-Patent Literature 15).

For sirtuins involved in senescence, it has been reported that their enhancement or suppression is caused by Chinese medicines and others, but they have not been tested as to whether they extend longevity. On the other hand, resveratrol, which is contained in red grapes, has been reported to extend the longevity of fruit flies and mice.

Besides the above, there have been many reports on retarding senescence or extending longevity. For example, it has been disclosed that application of a substance inhibiting the expression or function of a gene encoding G protein γ subunit 11 makes it possible to inhibit cellular aging (Patent Literature 1). In addition, it has been reported that alkyl resorcinols having a specified structure have an action of activating sirtuins and an action of retarding senescence, and exhibit an effect of extending the longevity of individuals (Patent Literature 2). Furthermore, it has been disclosed that royal jelly, heterocyclic compounds with a specified structure, resveratrol, an extract from grape leaves, active carbon, an extract from Chinese redbud (*Cercis chinensis*), curcuminoids, a kudzu (*Pueraria lobata*) extract, and others exhibit an action of preventing senescence, an action of extending longevity, and the like (Patent Literatures 3 to 10).

However, the fact is that there are little reports on foods, medicaments, and others exerting on mammalian animals both an effect of delaying the onset of senescence symptoms and an effect of extending longevity as an extension of senescence.

CITATION LIST

Patent Literature

Patent Literature 1: WO 2007/102572
Patent Literature 2: JP 2013-249260 A
Patent Literature 3: JP 2012-207004 A
Patent Literature 4: JP 2008-94795 A
Patent Literature 5: JP 2007-145809 A
Patent Literature 6: JP 2010-208969 A
Patent Literature 7: JP 2006-515590 A
Patent Literature 8: JP 2008-120726 A
Patent Literature 9: JP 2010-270012 A
Patent Literature 10: JP 2012-246242 A Non-Patent Literature Non-Patent Literature 1: A. Dillin et al., "Rate of behavior and aging specified by mitochondrial function during development", Science 298, 2398-2401 (2002)
Non-Patent Literature 2: Grandison RC1, Piper M D, Partridge L., "Amino-acid imbalance explains extension of life span by dietary restriction in Drosophila", Nature 462, 1061-1064 (2009)
Non-Patent Literature 3: "Understanding studies on aging", edited by Toshinori Ide, published by Yodosha Co., Ltd., 2002, pages 25,
Non-Patent Literature 4: Coleman R. J. et al, "Carolic restriction delays disease onset and mortality in Rhesus monkeys", Science 325, 201-204 (2009)
Non-Patent Literature 5: "Calorie restriction mimetics", Takuya Chiba, Isao Shimokawa, Zikken Igaku Zoukan [Experimental Medicine (extra number)], Vol. 31, No. 20, 182-189 (2013)
Non-Patent Literature 6: "Insulin and IGF-1 signals and control of aging and longevity", Kohjiro Ueki, Zikken Igaku Zoukan [Experimental Medicine (extra number)], Vol. 31, No. 20, 22-27 (2013)
Non-Patent Literature 7: "Resveratrol improves health and survival of mice on a high-calorie diet", Bauer et al., Nature, 477:337-342 (2006)
Non-Patent Literature 8: "Effect of A Red Wine-derived Polyphenol Protocatechuic Acid on the Lifespan of Drosophila Melanogaster", Yuzo Yagi, et al., Food Function 11, 9-13 (2013).
Non-Patent Literature 9: "Small molecule modulators of sirtuins" [in Japanese translation], D. A. Sinclair, B. P. Hubbard, Zikken Igaku Zoukan [Experimental Medicine (extra number)], Vol. 31, No. 20, 209-217 (2013)
Non-Patent Literature 10: "Science of aging and longevity", Zikken Igaku Zoukan [Experimental Medicine (extra number)], Vol. 31, No. 20 (2013), edited by Shin-ichiro Imai and Jun Yoshino, Yodosha Co., Ltd.
Non-Patent Literature 11: Hoeijmakers, J. H. J., "Genome maintenance mechanisms for preventing cancer", Nature, 411:366-374, 2001
Non-Patent Literature 12: Akihiro Ito, "Benefits of miso removing radioactive substances—a physiological effect by miso of preventing cancer", In "Forefront of miso science", 1999, published by Japan Miso Promotion Board
Non-Patent Literature 13: "The defensive effects of a fermented vegetable product on X-ray exposure—effects on the regeneration of intestinal crypts", Ashida et al., The Journal of Japan Mibyou System, 12(1), 129-130 (2006)
Non-Patent Literature 14: "Reduced coenzyme Q10 supplementation decelerate senescence in SAM-P1 mice", J. Yan et. al., Experimental Gerontology, 41 (2006), 130-140
Non-Patent Literature 15: "Effect of chronic feeding of soy protein isolate on the advance of senescence in the senescence accelerated mouse (SAM)", Atsuko Kohno et al., Nutr. Sci. Soy Protein, Jpn: 7, 25-29 (1986)
Non-Patent Literature 16: "Analysis of aging", Sumino Yanase, Naoaki Ishii, In "Nematodes Labo Manual", edited by Shohei Mitani, pp. 201-206 (2003), Springer-Verlag Tokyo, Inc.

SUMMARY OF INVENTION

Technical Problem

In light of the above situation, an object of the present invention is to provide a senescence retarding agent that delays the onset of a plurality of senescence-related symptoms and extends longevity, and has high safety.

Solution to Problem

The present inventors have made extensive research in order to achieve the above-described object, with the result that a fermentation product in which a plurality of plants having an experience of being eaten have been fermented by lactic acid bacteria and yeasts, koji mold, and others retards a variety of senescence symptoms associated with aging and exhibits an effect of prolonging survival, whereby the present invention has been reached.

Accordingly, the present invention is directed to a senescence retarding agent characterized by containing a plant fermentation product as an active ingredient, the plant fermentation product being a mixture of the following:

(a) a koji mold-fermented product of one or more kinds of beans and/or cereals selected from the group consisting of barley, black soybean, red rice, black rice, adzuki bean, adlay, Japanese millet, foxtail millet, and millet;

(b) a yeast- and/or lactic acid bacterium-fermented product of one or more kinds of fruits selected from the group consisting of mikan (mandarin orange), grape, apple, yamabudo (crimson glory grape), peach, kaki (Japanese persimmon), papaya, nashi (Japanese pear), watermelon, ume (Japanese apricot), fig, karin (Chinese quince), pumpkin, kumquat, yuzu (Chinese lemon), loquat, apricot, jujube, chestnut, matatabi (silvervine), and sumomo (Japanese plum);

(c) a yeast- and/or lactic acid bacterium-fermented product of one or more kinds of root crops and/or potatoes selected from the group consisting of murasaki-imo (purple sweet potato), kikuimo (Jerusalem artichoke), carrot, onion, satsuma-imo (sweet potato), satoimo (taro), jinenzyo (Japanese yam), daikon (Japanese radish), akakabu (red turnip), gobo (burdock root), renkon (lotus root), yacon, yuri-ne (lily bulb), kuwai (arrowhead), ginger, garlic, and turmeric;

(d) a yeast- and/or lactic acid bacterium-fermented product of one or more kinds of flowers and/or leaf vegetables selected from the group consisting of cabbage, shiso (perilla), mulberry leaves, dokudami (Korean houttuynia), yomogi (wormwood), kumazasa (kuma bamboo grass), and dandelion;

(e) a yeast- and/or lactic acid bacterium-fermented product of one or more kinds of seaweeds selected from the group consisting of kombu (sea tangle), wakame (*Undaria pinnatifida*), and mozuku (*Nemacystus decipiens*);

(f) a yeast- and/or lactic acid bacterium-fermented product of one or more kinds of seeds selected from the group consisting of black sesame seeds, walnuts, and ginkgo nuts; and (g) a yeast- and/or lactic acid bacterium-fermented product of one or two kinds of mushrooms selected from the group consisting of maitake (*Grifola frondosa*) and shiitake (*Lentinus edodes*).

The present invention is also directed to a food or drink containing the above-described senescence retarding agent.

In addition, the present invention is directed to a longevity extending agent containing, as active ingredients, the plant fermentation products according to the above (a) to (g).

Advantageous Effects of Invention

The senescence retarding agent of the present invention can retard the onset of a variety of senescence symptoms associated with aging of animals and at the same time, prolong their survival. In addition, any of the plants and microorganisms that can be used as raw materials for plant fermentation products that are used as active ingredients has accumulated experience as a food, and thus is of extremely high safety.

DESCRIPTION OF EMBODIMENTS

Figure 1:
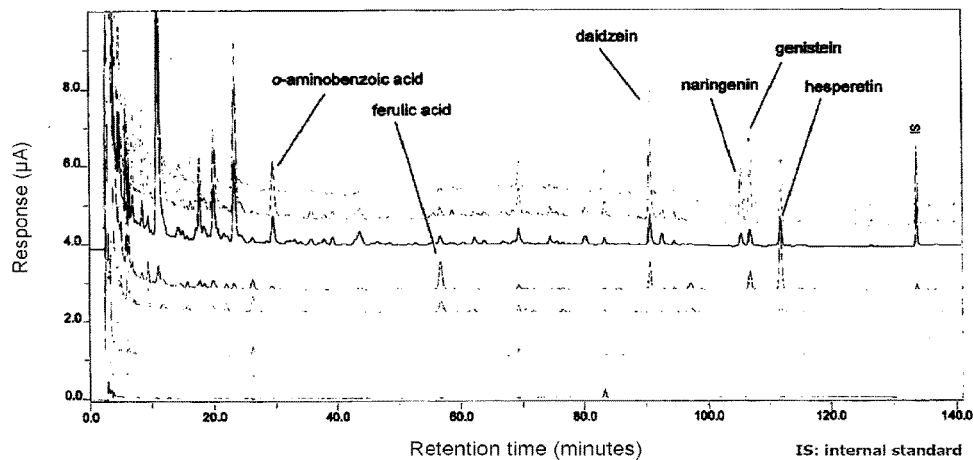
FIG. 1 shows the result of HPLC analysis of polyphenols contained in a plant fermentation product of Production Example 2.

A senescence retarding agent of the present invention contains, as an active ingredient, a plant fermentation product defined below. The plant fermentation product is a mixture of plant fermentation products (a) to (g) described below.

(a) a fermentation product obtained by subjecting a koji mold to treatment of one or more kinds beans and/or cereals selected from the group consisting of barley, black soybean, red rice, black rice, adzuki bean, adlay, Japanese millet, foxtail millet, and millet.

(b) a fermentation product obtained by subjecting a yeast and/or lactic acid bacterium to treatment of one or more kinds of fruits selected from the group consisting of mikan (mandarin orange), grape, apple, yama-budo (crimson glory grape), peach, kaki (Japanese persimmon), *papaya*, nashi (Japanese pear), watermelon, ume (Japanese apricot), fig, karin (Chinese quince), pumpkin, kumquat, yuzu (Chinese lemon), loquat, apricot, jujube, chestnut, matatabi (silvervine), and sumomo (Japanese plum).

(c) a fermentation product obtained by subjecting a yeast and/or lactic acid bacterium to treatment of one or more kinds of root crops and/or potatoes selected from the group consisting of murasaki-imo (purple sweet potato), kikuimo (Jerusalem artichoke), carrot, onion, satsuma-imo (sweet potato), satoimo (taro), jinenzyo (Japanese yam), daikon (Japanese radish), akakabu (red turnip), gobo (burdock root), renkon (lotus root), yacon, yuri-ne (lily bulb), kuwai (arrowhead), ginger, garlic, and turmeric.

(d) a fermentation product obtained by subjecting a yeast and/or lactic acid bacterium to treatment of one or more kinds of flowers and/or leaf vegetables selected from the group consisting of cabbage, shiso (*perilla*), mulberry leaves, dokudami (Korean houttuynia), yomogi (wormwood), kumazasa (kuma bamboo grass), and dandelion.

(e) a fermentation product obtained by subjecting a yeast and/or lactic acid bacterium treatment of one or more kinds of seaweeds selected from the group consisting of kombu (sea tangle), wakame (*Undaria pinnatifida*), and mozuku (*Nemacystus decipiens*).

(f) a fermentation product obtained by subjecting a yeast and/or lactic acid bacterium to treatment of one or more kinds of seeds selected from the group consisting of black sesame seeds, walnuts, and ginkgo nuts.

(g) a fermentation product obtained by subjecting a yeast and/or lactic acid bacterium to treatment of one or two kinds of mushrooms selected from the group consisting of maitake (*Grifola frondosa*) and shiitake (*Lentinus edodes*).

In the senescence retarding agent of the present invention, a plant fermentation product having the above-described fermentation products (a) to (g) mixed may be directly used as the active ingredient, and can be subjected to an additional multistage fermentation, thereby resulting in improved taste and formulability of preparations.

As the yeast, there are included yeasts of species belonging to, for example, the genera *Saccharomyces* and *Zygosaccharomyces*. Among these yeast species, use is made preferably of, for example, *Saccharomyces cerevisiae* (*S. cerevisiae*), *Zygosaccharomyces rouxii* (*Z. rouxii*), and *Saccharomyces exiguss* (*S. exiguus*). As the lactic acid bacterium, there are included, for example, lactic acid bacteria of species belonging to the genera *Pediococcus, Leuconostoc, Lactobacillus*, and *Lactococcus*. Among these species, use is made preferably of, for example, *Pediococcus acidilacti* (*P. acidilacti*), *Lactobacillus brevis* (*L. brevis*), *Leuconostoc mesenteroides* (*L. mesenteroides*), *Lactobacillus plantarum* (*L. plantarum*), *Lactococcus lactis* (*L. lactis*), *Lactobacillus sakei* (*L. sakei*), *Pediococcus pentosaceus* (*P. pentosaceus*), *Lactobacillus casei* (*L. casei*), *Lactobacillus reuteri* (*L. reuteri*), and *Lactobacillus curvatus* (*L. curvatus*). One or more of these species can be used. Examples of the koji mold include, for example, *Aspergillus oryzae, Aspergillus niger*, and *Aspergillus kawachii*, and one or more of these species can be used. Strains of the above-mentioned species that are commercially available can also be used.

The plants, such as beans/cereals and fruits, that are to be fermented may be used as they are, or alternatively may optionally be subjected to pretreatment such as chopping and drying. Water may be added for dilution, if necessary.

The above-described fermentation products (a) to (g) are obtained by adding a lactic acid bacterium, yeast, or koji mold to plants to be used as raw materials and culturing the mixture. The culturing can be carried out in routine procedures. For example, it is possible that to a mixture of one or more kinds of plants is added a lactic acid bacterium, yeast, or koji mold in an amount of about 0.001 to 1 mass %, and the mixture is subjected to fermentation at 20 to 50° C. for a period of time in the order of 70 to 140 hours.

The fermentation products (a) to (g) thus obtained can be mixed and directly used as the active ingredient, though it is preferable that they are optionally further cultured at 20 to 40° C. for a period of time in the order of 200 to 300 hours. Furthermore, the mixture is preferably subjected to after-fermentation (aging). The after-fermentation may optionally be carried out using an acetic acid bacterium. For example, to a material in which one or more of the plants contained in the above (a) to (g) have been subjected to treatment with the above-mentioned yeast may be added an acetic acid bacterium-fermented product in which an acetic acid bacterium, such as *Acetobacter aceti*, has been used for the fermentation. The after-fermentation may be performed at 25 to 35° C. for a period of time in the order of 70 hours to about 1 year. The aging process by the after-fermentation makes it possible to result in improved taste and formulability of preparations, and also increased antioxidant activity.

An example of preferable methods for producing the plant fermentation product is a multistage, combined fermentation process. This process is a process in which combined lactic acid bacterium-fermented product of fruits, vegetables, and seaweeds as their respective main raw material, and yeast fermentation products of vegetables, root crops, seeds, mushrooms, and fruits as their respective main raw material are mixed, and to the mixture is added a koji mold-fermented product of cereals and beans as the main raw material, followed by addition of an acetic acid bacterium-fermented product, to make a mixture, which is then filtrated and concentrated, followed by being subjected to an additional after-fermentation for a period of time in the order of about 1 year. It would be believed that by this multistage, combined fermentation, each of the fermentation products undergoes further assimilation and conversion by bacteria of different species, thereby resulting in not only an improved flavor, but also an enhancement of effects such as antioxidant activity.

A senescence retarding agent and a longevity extending agent of the present invention are obtained by adding pharmacologically acceptable carriers, excipients, water activity adjusting agents, and others to the thus prepared plant fermentation product according to known pharmaceutical methods and formulating the mixture into preparations. The plant fermentation product may be optionally concentrated to adjust its concentration or formed into powder by spraying or freeze drying. Carriers and excipients that are used in the formulation include, for example, lactose, glucose, saccharose, starch, and sugar mixtures. The senescence retarding agent and the longevity extending agent are used in final forms of solutions, pastes, soft capsules, chewable tablets, and capsules. As for dosage and usage, the senescence retarding agent and the longevity extending agent can be orally taken, for example, in an amount in the order of 0.1 to 10 g, preferably 0.6 to 6 g, (in terms of solids) per day for an adult, as the plant fermentation product that is used as the active ingredient.

A senescence retarding and longevity extending agent of the present invention can be processed into the form of foods or drinks by combining it with known food materials, in addition to medicaments, quasi-drugs, and the like. The above-described plant fermentation product can be taken as it is, and to improve its storability, may be sterilized, and then filtered and concentrated, or alternatively may be formed into powder by optionally adding an excipient and subjecting the mixture to spraying or freeze-drying. Furthermore, it is desirable that a senescence retarding and longevity extending agent of the present invention is concentrated to reduce the water activity, in order to improve the shelf life in a distribution process. Examples of forms of such food and drinks can be pastes, soft capsules, tablets, health drinks, and others. A superior effect of retarding senescence can be achieved by taking it in an amount in the order of 0.1 to 10 g, preferably 0.6 to 6 g, (in terms of solids) per day for an adult, as the plant fermentation product. Products available on the market in which a plant fermentation product as described above has been formulated into preparations and is in the form of food include, for example, Amou koso kin-jirushi, Amou koso capsules (manufactured by Nihon Sizen Hakkoh).

The plant fermentation product, i.e., the active ingredient, that is used in the present invention has properties (1) to (4) described below:

(1) Taste

The plant fermentation product has a sweetness derived from rice malt, in addition to a sweet taste and organic acids derived from raw materials such as fruits and vegetables. It contains polyphenols derived from raw materials, and yet is slightly bitter in taste.

(2) Solubility in Water

The plant fermentation product is easily soluble in water.

(3) Stability

The plant fermentation product is stable against heat and acid, and pastes thereof are not decomposed or changed in taste even after being stored at room temperature for 1 year.

(4) Safety

The vegetables, fruits, herbs, and others that are used as raw materials are ones that have been eaten daily, and the yeast, lactic acid bacterium, and koji mold strains that are used in the fermentation all employ ones that have been used in food brewing or fermenting or are derived from tsukemonos (Japanese pickled vegetables), and thus these materials and strains have rich history of use in foods.

The plant fermentation product that is used in the present invention also has properties described below.

(i) Nutriential Ingredients (Per 100 g of Plant Fermentation Product)

| | |
|---|---|
| Moisture | 15 to 35 g |
| Protein | 5 to 20 g |
| Total fat | 1 to 8 g |
| Ash | 1 to 5 g |
| Available carbohydrates | 30 to 70 g |
| Sodium | 40 to 150 mg |
| Vitamin B6 | 0.1 to 0.5 mg |
| Energy | 200 to 500 kcal |

(ii) Amino Acid Composition (Per 100 g of Plant Fermentation Product)

| | |
|---|---|
| Arginine | 0.2 to 0.6 g |
| Lysine | 0.1 to 0.7 g |
| Histidine | 0.1 to 0.4 g |
| Phenylalanine | 0.2 to 0.8 g |
| Tyrosine | 0.1 to 0.6 g |
| Leucine | 0.3 to 1.2 g |
| Isoleucine | 0.2 to 0.8 g |
| Methionine | 0.05 to 0.3 g |
| Valine | 0.2 to 0.9 g |
| Alanine | 0.2 to 0.9 g |
| Glycine | 0.2 to 0.7 g |
| Proline | 0.4 to 1.2 g |
| Glutamic acid | 1.2 to 3.0 g |
| Serine | 0.2 to 0.8 g |
| Threonine | 0.2 to 0.7 g |
| Aspartic acid | 0.4 to 1.5 g |
| Tryptophan | 0.03 to 0.15 g |
| Cystine | 0.05 to 0.40 g |

(iii) Organic Acid Composition (Per 100 g of Plant Fermentation Product)

| | |
|---|---|
| Citric acid | 0.5 to 1.2 g |
| Malic acid | 0.05 to 0.5 g |
| Succinic acid | 0.04 to 0.3 g |
| Lactic acid | 0.5 to 6.0 g |
| Formic acid | 0.01 to 0.1 g |
| Pyruvic acid | 0.005 to 0.05 g |
| Free γ-aminobutyric acid | 0.01 to 0.05 g |

(iv) Mineral Composition (Per 100 g of Plant Fermentation Product)

| | |
|---|---|
| Phosphorus | 100 to 400 mg |
| Iron | 1 to 5 mg |
| Calcium | 500 to 900 mg |
| Potassium | 600 to 1000 mg |
| Magnesium | 70 to 120 mg |
| Zinc | 0.8 to 1.6 mg |
| Iodine | 1.0 to 2.5 mg |

(v) Polyphenols (μg/g of Plant Fermentation Product)

| | |
|---|---|
| Caffeic acid | 20 to 50 |
| o-aminobenzoic acid | 10 to 25 |
| Ferulic acid | 40 to 70 |
| p-Coumaric acid | 15 to 40 |
| Daizein | 40 to 65 |
| Genistein | 65 to 90 |
| Glycitein | 2 to 8 |
| Quercetin | 3 to 12 |
| Hesperetin | 200 to 300 |
| Naringenin | 30 to 60 |

(vi) Resveratrol

The total of the contents of the trans and cis forms of resveratrol is not more than 0.1 mg/g.

A senescence retarding agent containing the plant fermentation product as the active ingredient improves the survival rate of oxygen-sensitive nematodes and senescence accelerated mice in a dose-dependent manner, and at the same time, exhibits an effect of delaying the onset of senescence symptoms in the behavior, skin, eye, and backbone associated with aging of senescence accelerated mice.

EXAMPLES

The present invention is now described in more detail with reference to Examples and others, and is not limited thereto at all.

Production Example 1

Production of Plant Fermentation Product (1):

As raw materials, use was made of the following:

(a) beans and/or cereals (barley, black soybean, red rice, black rice, adzuki bean, adlay, Japanese millet, foxtail millet, and millet)

(b) fruits (mikan (mandarin orange), grape, apple, yamabudo (crimson glory grape), peach, kaki (Japanese persimmon), *papaya*, nashi (Japanese pear), watermelon, ume (Japanese apricot), fig, karin (Chinese quince), pumpkin, kumquat, yuzu (Chinese lemon), loquat, apricot, jujube, chestnut, matatabi (silvervine), and sumomo (Japanese plum))

(c) root crops (murasaki-imo (purple sweet potato), kikuimo (Jerusalem artichoke), carrot, onion, satsuma-imo (sweet potato), satoimo (taro), Japanese yam, daikon (Japanese radish), akakabu (red turnip), gobo (burdock root), renkon (lotus root), yacon, yuri-ne (lily bulb), kuwai (arrowhead), ginger, garlic, and turmeric)

(d) flowers and/or leaf vegetables (cabbage, shiso (*perilla*), mulberry leaves, dokudami (Korean houttuynia), yomogi (wormwood), kumazasa (kuma bamboo grass), and dandelion)

(e) seaweeds (kombu (sea tangle), wakame (*Undaria pinnatifida*), and mozuku (*Nemacystus decipiens*))

(f) seeds (black sesame seeds, walnuts, and ginkgo nuts)

(g) mushrooms (maitake (*Grifola frondosa*) and shiitake (*Lentinus edodes*))

To each (730 kg) of the above-described raw materials (c), (d), and (g) was added 0.2 mass % of each of cultures of lactic acid bacteria (*P. acidilacti, L. brevis, L. mesenteroides, L. plantarum, L. lactis, L. sakei, L. casei*) that had been adjusted to have a cell concentration of about $1.0 \times 10^5$ cfu/g, and culturing was carried out at 30 °C. for 50 hours. To each (900 kg) of the above-described raw materials (b), (e), and (f) was added 0.4 mass % of each of cultures of yeasts (five species of *S. cerevisiae*, two species of *Z. rouxii*) that had been adjusted to have a cell concentration of about $1.0 \times 10^5$ cfu/g, and culturing was carried out at 30 °C. for 50 hours. To a raw material derived from (a) beans and cereals (1000 kg) was added 0.1 mass % of each of koji molds (yellow koji mold, black koji mold, white koji mold), and culturing was carried out at 35° C. for 70 hours. Subsequently, these cultured products were mixed, and the mixture was subjected to culturing at 30° C. for 200 hours. The moromi (unrefined fermented product) after ending the fermentation was subjected to solid-liquid separation, and the resulting filtrate was concentrated to a paste, which was poured into containers, followed by an additional after-fermentation (aging) for one year to obtain a plant fermentation product.

The plant fermentation product obtained in Production Example 1 had properties described below:

(i) Nutriential Ingredients (Per 100 g of Plant Fermentation Product)

| | |
|---|---|
| Moisture | 25.2 g |
| Protein | 11.8 g |
| Total fat | 3.6 g |
| Ash | 2.1 g |
| Available carbohydrates | 57.3 g |
| Sodium | 54.0 mg |
| Vitamin B6 | 0.20 mg |
| Energy | 309 kcal |

(ii) Amino Acid Composition (Per 100 g of Plant Fermentation Product)

A sample was hydrolyzed with 6 N hydrochloric acid, and then analyzed with an automatic amino acid analyzer. For cystine, a sample was subjected to performic acid oxidation treatment, followed by hydrochloric acid hydrolysis. Tryptophan was analyzed using a high performance liquid chromatography method.

| | |
|---|---|
| Arginine | 0.33 g |
| Lysine | 0.34 g |
| Histidine | 0.22 g |
| Phenylalanine | 0.51 g |
| Tyrosine | 0.32 g |
| Leucine | 0.74 g |
| Isoleucine | 0.42 g |
| Methionine | 0.13 g |
| Valine | 0.54 g |
| Alanine | 0.48 g |
| Glycine | 0.42 g |
| Proline | 0.92 g |
| Glutamic acid | 2.25 g |
| Serine | 0.4 g |
| Threonine | 0.36 g |
| Aspartic acid | 0.84 g |
| Tryptophan | 0.06 g |
| Cystine | 0.15 g |

(iii) Organic Acid Composition (Per 100 g of Plant Fermentation Product)

| | |
|---|---|
| Citric acid | 0.81 g |
| Malic acid | 0.31 g |
| Succinic acid | 0.12 g |
| Lactic acid | 1.17 g |
| Formic acid | 0.03 g |
| Pyruvic acid | 0.01 g |
| Free γ-aminobutyric acid | 24 mg |

(iv) Mineral Composition (Per 100 g of Plant Fermentation Product)

| | |
|---|---|
| Phosphorus | 262 mg |
| Iron | 2.65 mg |
| Calcium | 72.1 mg |
| Potassium | 798 mg |
| Magnesium | 97.8 mg |
| Zinc | 1.19 mg |
| Iodine | 1.7 mg |

Production Example 2

Production of Plant Fermentation Product (2):

As raw materials, use was made of the following:

(a) beans and/or cereals (barley, black soybean, red rice, black rice, adzuki bean, adlay, Japanese millet, foxtail millet, and millet)

(b) fruits (mikan (mandarin orange), grape, apple, yamabudo (crimson glory grape), peach, kaki (Japanese persimmon), *papaya*, nashi (Japanese pear), watermelon, ume (Japanese apricot), fig, karin (Chinese quince), pumpkin, kumquat, yuzu (Chinese lemon), loquat, apricot, jujube, chestnut, matatabi (silvervine), and sumomo (Japanese plum))

(c) root crops (murasaki-imo (purple sweet potato), kikuimo (Jerusalem artichoke), carrot, onion, satsuma-imo (sweet potato), satoimo (taro), Japanese yam, daikon (Japanese radish), akakabu (red turnip), gobo (burdock root), renkon (lotus root), yacon, yuri-ne (lily bulb), kuwai (arrowhead), ginger, garlic, and turmeric)

(d) flowers and/or leaf vegetables (cabbage, shiso (*perilla*), mulberry leaves, dokudami (Korean houttuynia), yomogi (wormwood), kumazasa (kuma bamboo grass), and dandelion)

(e) seaweeds (kombu (sea tangle), wakame (*Undaria pinnatifida*), and mozuku (*Nemacystus decipiens*))

(f) seeds (black sesame seeds, walnuts, and ginkgo nuts)

(g) mushrooms (maitake (*Grifola frondosa*) and shiitake (*Lentinus edodes*))

To each (730 kg) of the above-described raw materials (c), (d), and (g) was added 0.2 mass % of each of cultures of lactic acid bacteria (*P. acidilacti, L. brevis, L. mesenteroides, L. plantarum, L. lactis, L. sakei, L. casei*) that had been adjusted to have a cell concentration of about $1.0 \times 10^5$ cfu/g, and culturing was carried out at 30° C. for 50 hours. To each (900 kg) of the above-described raw materials (b), (e), and (f) was added 0.4 mass % of each of cultures of yeasts (five species of *S. cerevisiae*, two species of *Z. rouxii*) that had been adjusted to have a cell concentration of about $1.0 \times 10^5$ cfu/g, and culturing was carried out at 30° C. for 50 hours. To a raw material derived from (a) beans and cereals (500 kg) was added 0.1 mass % of each of koji molds (yellow koji mold, black koji mold, white koji mold), and culturing was carried out at 35° C. for 70 hours. Subsequently, these cultured products were mixed, and the mixture was subjected to culturing at 30° C. for 200 hours. The moromi (unrefined fermented product) after ending the fermentation was subjected to solid-liquid separation, and the resulting filtrate was concentrated to a paste, which was poured into containers, followed by an additional after-fermentation (aging) for one year to obtain a plant fermentation product.

The plant fermentation product obtained in Production Example 2 had properties described below:

(i) Nutriential Ingredients (Per 100 g of Plant Fermentation Product)

| | |
|---|---|
| Moisture | 31.7 g |
| Protein | 14.6 g |

| | |
|---|---|
| Total fat | 5.3 g |
| Ash | 2.8 g |
| Available carbohydrates | 40.4 g |
| Sodium | 59.6 mg |
| Vitamin B6 | 0.24 mg |
| Energy | 278 kcal |

(ii) Amino Acid Composition (Per 100 g of Plant Fermentation Product)

A sample was hydrolyzed with 6 N hydrochloric acid, and then analyzed with an automatic amino acid analyzer. For cystine, a sample was subjected to performic acid oxidation treatment, followed by hydrochloric acid hydrolysis. Tryptophan was analyzed using a high performance chromatography method.

| | |
|---|---|
| Arginine | 0.46 g |
| Lysine | 0.51 g |
| Histidine | 0.28 g |
| Phenylalanine | 0.63 g |
| Tyrosine | 0.43 g |
| Leucine | 0.97 g |
| Isoleucine | 0.58 g |
| Methionine | 0.16 g |
| Valine | 0.72 g |
| Alanine | 0.67 g |
| Glycine | 0.55 g |
| Proline | 0.98 g |
| Glutamic acid | 2.65 g |
| Serine | 0.59 g |
| Threonine | 0.51 g |
| Aspartic acid | 1.26 g |
| Tryptophan | 0.10 g |
| Cystine | 0.18 g |

(iii) Organic Acid Composition (Per 100 g of Plant Fermentation Product)

| | |
|---|---|
| Citric acid | 0.40 g |
| Malic acid | 0.10 g |
| Succinic acid | 0.08 g |
| Lactic acid | 4.17 g |
| Formic acid | 0.02 g |
| Pyruvic acid | 0.02 g |
| Free γ-aminobutyric acid | 31 mg |

(iv) Polyphenols (See FIG. 1; μg/g of Plant Fermentation Product)

| | |
|---|---|
| Caffeic acid | 36.9 |
| o-aminobenzoic acid | 17.0 |
| Ferulic acid | 54.2 |
| p-Coumaric acid | 28.2 |
| Daizein | 53.8 |
| Genistein | 79.8 |
| Glycitein | 4.6 |
| Quercetin | 7.8 |
| Hesperetin | 265.7 |
| Naringenin | 42.5 |

(HPLC Conditions)
Column: MCM (4.6×250 mm; 5 μm)
Column temperature: 35° C.
Mobile Phases:
Mobile phase A: 100 mM sodium phosphate/5% methanol
Mobile phase B: 100 mM sodium phosphate/60% acetonitrile/10% methanol Gradient Conditions:
a linear gradient from 0 to 6% mobile phase B, from t=0 to 45 min
a linear gradient from 6 to 14% mobile phase B, from t=45 to 60 min
a linear gradient from 14 to 30% mobile phase B, from t=60 to 90 min
a linear gradient from 30 to 40% mobile phase B, from t=90 to 120 min
a linear gradient from 40 to 77% mobile phase B, from t=120 to 140 min
an isocratic elution up to 85% mobile phase B for 100 min
Flow rate: 1.0 mL/min
Detector: CoulArray, Model 5600A
(Measurement Method)

About 80 mg of a sample was accurately weighed, to which 100 μL of an internal standard solution (17-α-estradiol, 100 μg/mL) was added, followed by addition of 5 mL of a 90% methanol solution, and the mixture was shaken for 10 min and then subjected to sonication extraction at 35° C. for 30 min. After the extraction, the mixture was centrifuged at 3000 rpm for 10 min on a centrifuge. Then, the supernatant was collected and concentrated under a nitrogen stream, and then adjusted to a volume of 2 mL using 0.1 M sodium acetate buffer. To 1 mL of the prepared solution was added 10 mg of a β-glycosidase-type enzyme, and the mixture was subjected to enzyme treatment at 43° C. for 2 hours. To the solution after the enzyme treatment was added 500 μL methanol, and the mixture was filtered through a 0.45 μm filter to prepare a test solution.

Figure 2:
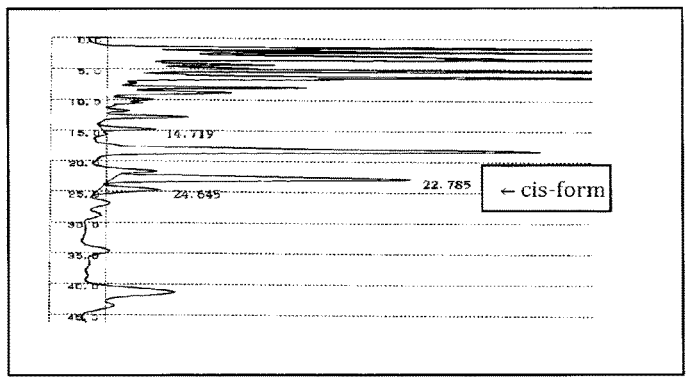
FIG. 2 shows the result of HPLC analysis of resveratrol contained in a plant fermentation product of Production Example 2.

(v) Resveratrol (See FIG. 2)

The plant fermentation product contains resveratrol in a total amount of trans and cis forms of 0.022 mg/g (trans form: 0.002 mg/g, cis form: 0.02 mg/g).

Detector: UV (310 nm)
Column: Nomura Chemical ODS-MG-3, 3×100 mm
Column temperature: 40° C.
Mobile phase: diluted phosphoric acid (1->500)/acetonitrile mixture (4:1)
Flow rate: 0.4 mL/min
(Measurement Method)

NSK Resveratrol (Standard Solution)

The content of one capsule (330 mg, corresponding to 3.3 mg resveratrol) was dissolved in 70% methanol to make a volume of 100 mL. The solution was filtered through a 0.45 μm membrane filter, and the filtrate was used as a standard solution.

Samples

About 1 g of a sample was dissolved in 30 mL water, to which 20 mL ethyl acetate was added, followed by mixing. The supernatant fluid was collected, and concentrated under reduce pressure. To the residue was added 5 mL of 70% methanol. The resulting solution was filtered through a 0.45 μm membrane filter, and the filtrate was used as a sample solution.

Resveratrol contained in red wine is known to have an anti-inflammatory action and a senescence retarding action or to extend the longevity of fruit flies. Since the plant fermentation product also exhibited a senescence retarding action and a longevity extending action in SAM mice, the content of resveratrol in the plant fermentation product was analyzed using an HPLC standard, in order to determine whether or not the resveratrol contributed to these actions. The result of HPLC analysis showed that the resveratrol contained 0.002 mg/g of the trans form and 0.02 mg/g of the cis form (the total amount of the trans and cis forms was 0.022 mg/g). It could not be expected that these concentrations lead to the senescence retarding effect and the longevity extending effect, and thus these effects of the plant fermentation product was believed to be attributed to a different substance(s).

Test Example 1

Longevity Extending Effect on Nematodes

Figure 3:
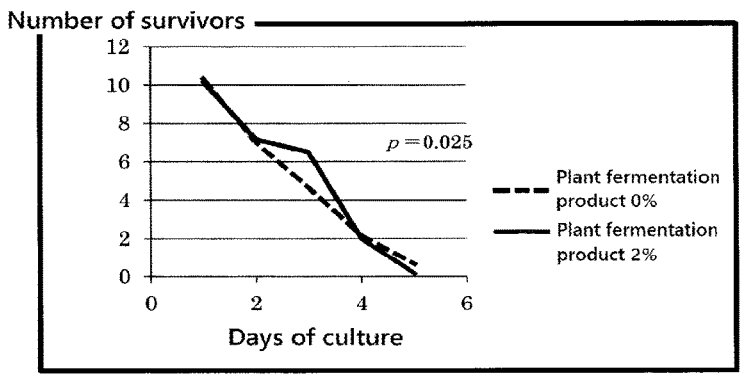
FIG. 3 represents a graph showing survival curves of oxygen-sensitive mutant (mev-1) nematodes under an atmosphere of 100% oxygen in Test Example 1. The ordinate represents the average number of survived nematodes per 3.5-cm Petri dish and the abscissa represents days of culture.

The plant fermentation product obtained in Production Example 1 was diluted in ion-exchanged water to prepare a 2% (w/w) solution, which was then sterilized in an autoclave at 121° C. for 20 min. Nematodes (*Caenorhabditis elegans*) used were of an oxygen-sensitive mutant strain (mev-1). mev-1 nematodes are prone to die when the oxygen concentration during the culture increases, resulting in shifting of their survival curves depending upon the oxygen concentration. It has been proved that this mutant strain has a mutation in succinate-ubiquinone dehydrogenase derived from a cytochrome b560 mutation in the complex II in the mitochondrial respiratory chain. In mev-1 nematodes that have been cultured for a long period and become aged, vacuoles are observed within the body, and furthermore, the accumulation of lipofuscin associated with aging is demonstrated. As mentioned, mev-1 mutant nematodes are experimental animals of a model suitable for studies on senescence. Survival curves were determined according to the method described by Ishii et al. (Non-Patent Literature 16). Specifically, 1 drop of a cultured broth after *Escherichia coli* strain K562 had been cultured with shaking in tryptone broth was added, using a Pasteur pipette, onto a tryptone agar medium (TN medium), which had been poured into Falcon plates of 3.5 cm diameter, and cultured overnight at 30° C. so as to form *Escherichia coli* mats having a diameter of about 5 mm. mev-1 nematodes were grown using, as prey, *Escherichia coli* cells that had been grown separately on a TN agar medium in a 9-cm diameter Petri dish. Out of these nematodes, nematodes at stage L4 were picked up, and transferred onto *Escherichia coli* mats in the 3.5-cm plate, in a total of 10 nematodes. Four 3.5-cm plates to which the nematodes had been transferred were placed into an air-tight bag, and then the atmosphere within the bag was 100% replaced with oxygen gas. On and after the next day, the number of living nematodes was daily determined under a stereomicroscope and recorded. After observation, the atmosphere was replaced again with oxygen gas in a similar way. As shown in FIG. 3, the resultant survival curves were shifted to the direction of a shorter longevity than that under conditions with a maximum of 80% oxygen saturation reported by Yanase and Ishii, which revealed that the experiments had been correctly performed. For the longevity of these oxygen-sensitive mutant nematodes under an atmosphere of 100% oxygen, the number of days of culture (age in days) at which a survival rate of 50% was given was about 3 days, which was shorter than that under an atmosphere of 80% oxygen reported by Ishii et al. (about 10 days), in comparison to the graph by Yanase and Ishii reported in their literature (Non-Patent Literature 16). The longevity extending effect was observed at a survival rate of around 50% in the group receiving 2% of the plant fermentation product, relative to the control group receiving water instead thereof. When a t-test was performed on these groups, this difference was found to be significant with a value of P=0.025. Since mev-1 mutant nematodes are known to be defective in the mitochondrial respiratory chain, it is strongly suggested that the toxicity is involved in active oxygen.

Test Example 2

For effects of the plant fermentation product on retarding senescence associated with aging, prolonging survival, and preventing the generation of projections in cases where senescence accelerated model mice (SAM mice) were used, examinations were carried out as follows. SAM mice (SAM-P1/SkuSlc, 10 weeks old, male), which had been propagated by Japan SLC, Inc., a breeder designated by the Council of SAM Research, was purchased therefrom. As feed, use was made of γ-ray sterilized solid chow pellets 500N, which were purchased from Sankyo Labo Service Corporation, Inc. SAM mice were kept individually in medium-sized polycarbonate cages manufactured by CLEA Japan, Inc., in which sterilized floor bedding had been placed, using a constant-temperature and constant-humidity equipment at 23±2° C. and 50±10% in an animal room dedicated to SPF animals. Lighting was switched off between 20:00 and 08:00. For comparison of projection formation, normal-type SAM-R1/SkuSlc mice were also kept in a similar manner.

The plant fermentation product obtained in Production Example 1 was diluted in ion-exchanged water to prepare 2% and 0.2% aqueous solutions as drinking water ad libitum. The feed used was γ-ray sterilized chow pellets 500N, which were purchased from Sankyo Labo Service Corporation, Inc. Each group contained 8 mice. When rearing was started, 4 mice were housed per cage, and then were gradually transferred to individual rearing. Four normal-type SAM-R1 mice were used, and were not administered with the plant fermentation product and were allowed to have free access only to ion-exchanged water. After the mice were transferred to individual rearing, their evaluation and observation were carried out and their cages were exchanged once a week. General observation items were body weight, amount of water drunk (=amount of sample intake), amount of feed taken, and appearance. For observation of senescence indexes, a standard evaluation system described in the evaluation instructions specified by the Council for SAM Research was employed, and the recording form used was one specified by the Council for SAM Research. In addition, mice were also measured for changes in the survival rate and for the size of a projection observable outside the surface of the body, which are not included in the evaluation system of the Council for SAM Research.

Senescence indexes specified by the Council for SAM Research are determined as described below:

Behavior (Two Items)

1. Reactivity (Grades 0-4)

Exploratory behavior observed when the mouse is out of its cage

0: The mouse behaves as in young mice.

1: The mouse walks on tiptoe (or scurries around) or is in an excited state.

2: The mouse slowly walks (sluggishly walks).

3: The mouse has no movement, but starts to move upon poking its rump.

4: The mouse has no movement at all.

2. Passivity (Grades 0-4)

Escape behavior when mild pressure is applied from directly above to the neck of the mouse 0: The mouse behaves as in young mice. The mouse makes a vigorous and slashing escape.

1: The mouse makes a slow escape.

2: The mouse does not make an escape.

3: The mouse does not make an escape. The mouse rolls over when being caught by the back of its neck and placed on the back 4: The mouse does not struggle upon catching its forelimb or hindlimb.

Gross Appearances (Nine Items)
Skin and Hair (Four Items)
3. Glossiness (Grades 0 - 4)
  Gloss of hair
  0 : Pure white and shiny (hair gloss displayed by young mice)
  1 : Between grades 0 and 2
  2 : Clearly lost gloss, but not dirty
  3 : Between grades 2 and 4
  4 : Very dirty
4. Coarseness (Grades 0-4)
  Stiff touch felt when the fur is rubbed with the fingertip
  Determination is made based on the area. Small ulcers or dermatitis is sometimes observed.
  0: No fluff ball is found. The hair is smooth and slippy.
  1: Fluff balls are observed on the head or face.
  2: Fluff balls extend to the shoulder.
  3: Fluff balls extend to the back.
  4: Fluff balls extend beyond the back and to the tail.
5. Loss of Hair (Grades 0-4)
  A state of the hair having become thin or of baldness. Since the abdominal region has thin hair, observation is made for the dorsal region. In pregnant mice, since the hair becomes thin, it is more preferable to determine an apparent baldness.
  0: No loss of hair is found at all
  1: A, baldness is observed in an approximate area corresponding to the head.
    B, a thin-hair region extends up to an about half of the entire back.
  2: A, baldness extends to not more than a quarter of the entire back.
    B, a thin-hair region extends to not less than a half of the entire back.
  3: Baldness extends roughly to not less than a quarter of and not more than a half of the entire back.
  4: Baldness extends to not less than a half of the entire back.
6. Skin Ulcers (Grades 0-4)
  White scars are also included. The whole body is inspected for scars.
  0: None
  1: Ulcers with scars (where the skin thickens in white) or crusts, regardless of their size.
  2: Oozily and reddish inflamed ulcers, of which the area is roughly not more than the area of the head.
  3: Oozily and reddish inflamed ulcers, of which the area is roughly not less than the area of the head and not more than a half of the area of the back.
  4: Oozily and reddish inflamed ulcers, of which the area is roughly not less than a half of the area of the back.
Eyes (Four Items)
  The right and left eyes are evaluated separately. The scores for the respective eyes are simply added into the Total Score. If necessary, a factor of ½ can be applied, or an item(s) that is/are easy to be evaluated can be employed. Direct observation of corneal lesions or cataract is done using a penlight.
7. Periophthalmic Lesions (Grades 0-3)
  0: No change. The eye is wide open.
  1: The eyelid becomes swollen and the eye is closed, or erosion occurs only around the eye.
  2: Erosion around the eye extends to the muffle.
  Note that although the eye does not have any lesion, ulcer is present only at the muffle.
  3: Erosion spreads over the face.
8. Corneal Opacity (Grades 0-3)
  Cloudy cornea. The cornea becomes cloudy, but its surface is smooth.
  A state as in kuzu-manju (a sweet bean paste ball covered in clear arrowroot gel) which has become white after putting it into a refrigerator.
  0: No lesion is found.
  1: The iris is visible.
  2: Although the iris is not visible, the reflection from the retina (a golden to orange color) is observed.
  3: No reflected light is observed.
9. Ulcers of Cornea (Grades 0-3)
  The cornea has become cloudy and its surface is rough.
  0: No lesion is found.
  1: A linear cloudiness is observed at a location corresponding to the optic fissure.
  2: Between grades 1 and 3. Light reflected from the circumference is observed.
  3: The ulcer spreads almost over the entire cornea and light reflected from the retina is not observed.
10. Cataract (Grades 0-2)
  Cataract. Cloudiness is reflected inside the eye through the transparent cornea. When viewed laterally, the cornea is found to be transparent.
  0: No cloudiness is observed. Light reflected from the retina is normal.
  1: Reflected light is slightly attenuated.
  2: No reflection occurs. (A golden to orange color is not observed.)
Spine (One Item)
11. Lordokyphosis (Grades 0-3)
  When stroking the back of the mouse, the finger gets stuck at the neck.
  The posture of the mouse is set so as to cause the neck to stretch.
  0: The finger does not get stuck at the neck.
  1: When gently stroking the back, the finger gets stuck at the neck; when strongly stroking the back, the finger does not get stuck at the neck.
  2: Even when strongly stroking the back, the finger gets stuck at the neck. When the back is straightened by pulling the tail, the finger does not get suck at the neck.
  3: The finger inevitably gets stuck at the neck.
Total Score
  For an individual mouse being evaluated, scores for the respective items are simply added up to produce its senescence evaluation score. If an eyelid is closed, then saline is drawn into a syringe and the eye is washed with the saline, so that the eye can be allowed to be opened; this procedure will be more invasive. If a mouse have a severe corneal lesion and cataract cannot be observed, then such a mouse has to be strictly omitted for analysis.
  The respective mice were evaluated once a week according to the above-described evaluation method for the degree of senescence defined by the Council for SAM Research, and results were reported on the form specified by the Council for SAM Research. At the same time, body weight measurements were carried out and the amounts of water drunk (sample intake) and feed taken were recorded. Although not included in the evaluation method specified by the Council for SAM Research, the survival and survival curve of mice were recorded, and from an age of 60 weeks onward, the major diameter, minor diameter, and height of a lymphomatoid projection which frequently occurred in the groin were measured to determine and record the projection volume (mm³).

Figure 4:
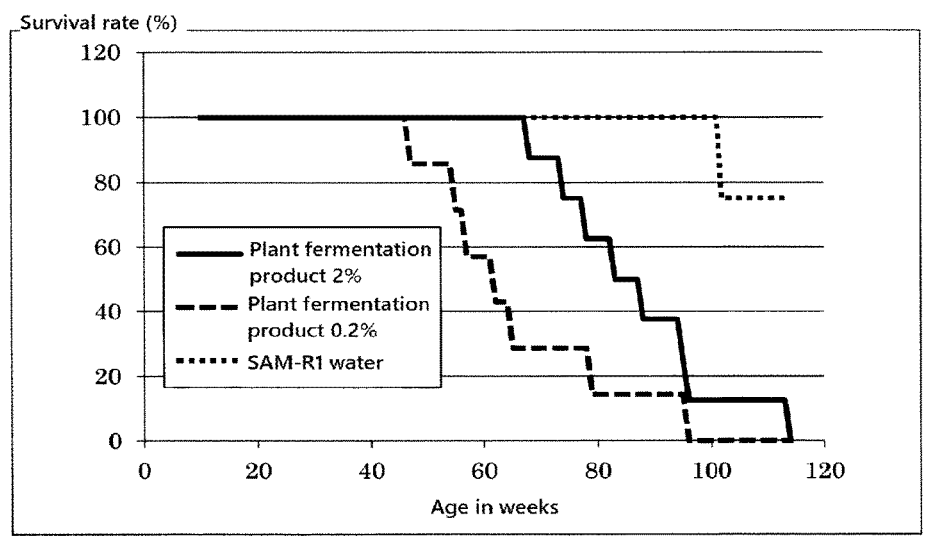
FIG. 4 represents a graph showing survival curves of SAM mice in Test Example 2. The ordinate represents the survival rate (%) and the abscissa represents the age in weeks, of SAM mice.
Figure 5:
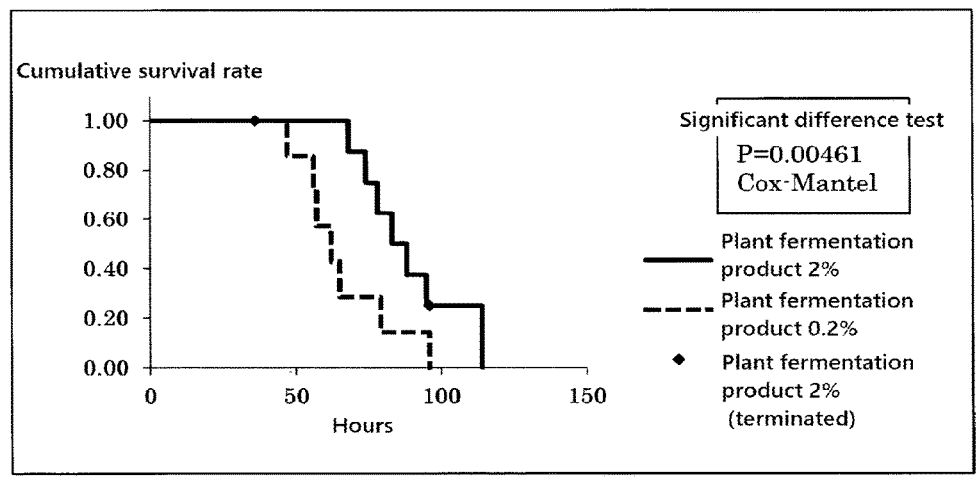
FIG. 5 represents a graph showing the result of significant difference test by Kaplan-Meier analysis of survival rates in examinations with administration of 2% and 0.2% of the plant fermentation product in Test Example 2. The ordinate represents the cumulative survival rate and the abscissa represents the age in weeks of mice. The solid line represents a survival curve for a group receiving 2% of the plant fermentation product, and the broken line for a group receiving 0.2% of the plant fermentation product.
Figure 6:
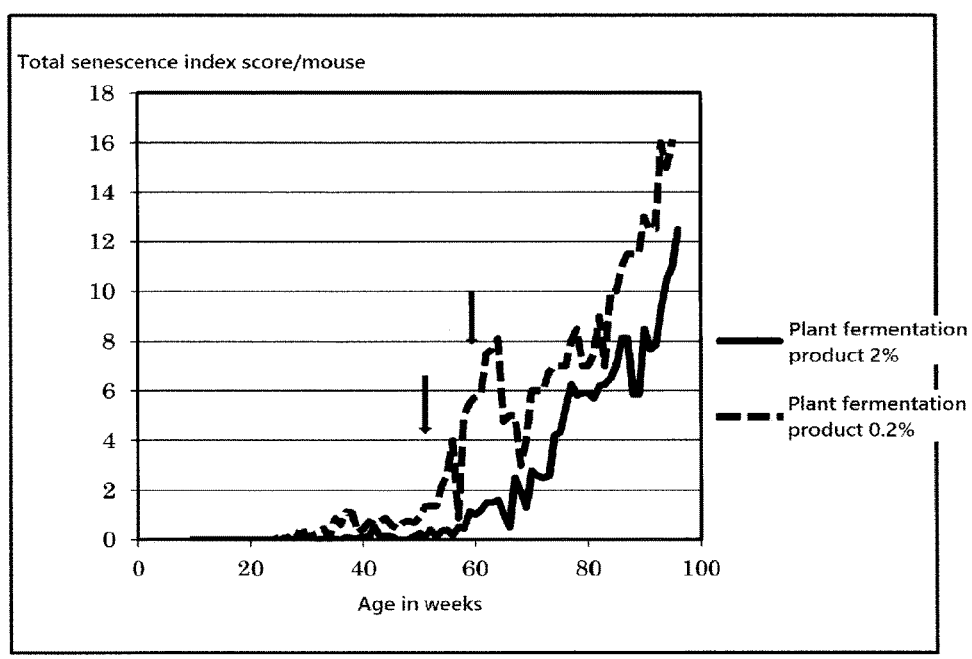
FIG. 6 represents a graph showing changes in the total evaluation score for the degree of senescence using a standard method defined by the Council for SAM Research in Test Example 2. The ordinate represents the total senescence index score per mouse and the abscissa represents the age in weeks. The solid line represents a group receiving 2% of the plant fermentation product, and the broken line a group receiving 0.2% of the plant fermentation product. In order to perform a significant difference test, two time-points at ages of 54 and 60 weeks at which 6 or more, out of 8, mice were allowed to be maintained alive were selected and are indicated by an arrow.
Figure 7:
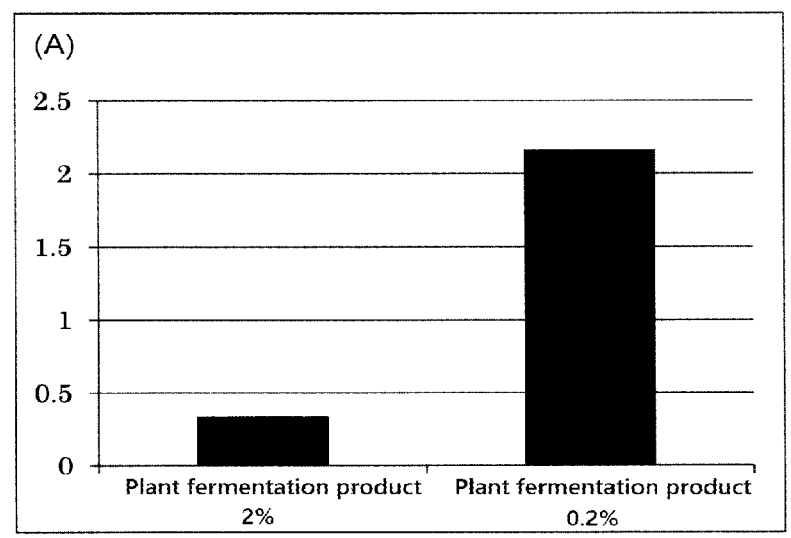
FIG. 7 represents graphs in which the total evaluation score for the degree of senescence were compared between groups receiving 2% and 0.2% of the plant fermentation product, at ages of 54 weeks (A) and 60 weeks (B) in Test Example 2.
Figure 7:
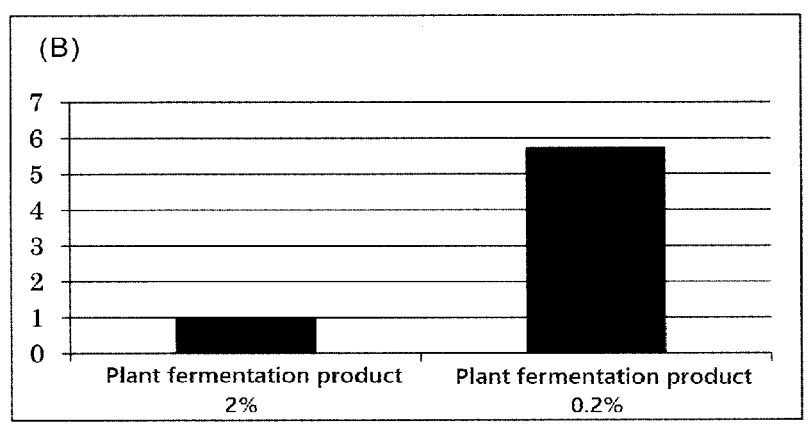
Figure 8:
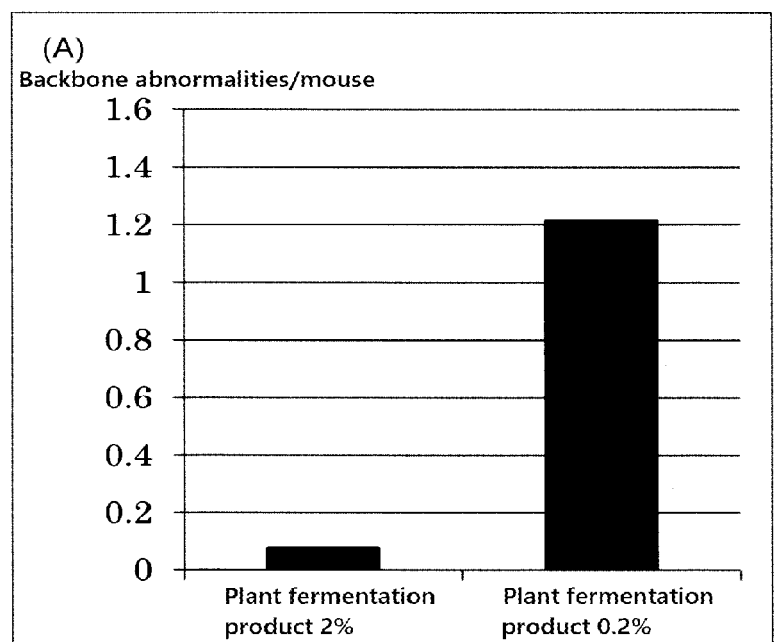
FIG. 8 represents graphs in which the "backbone curvature score" for the plant fermentation products, a senescence index, were compared between groups receiving 2% and 0.2% of the plant fermentation product, at ages of 54 weeks (A) and 60 weeks (B) in Test Example 2.
Figure 8:
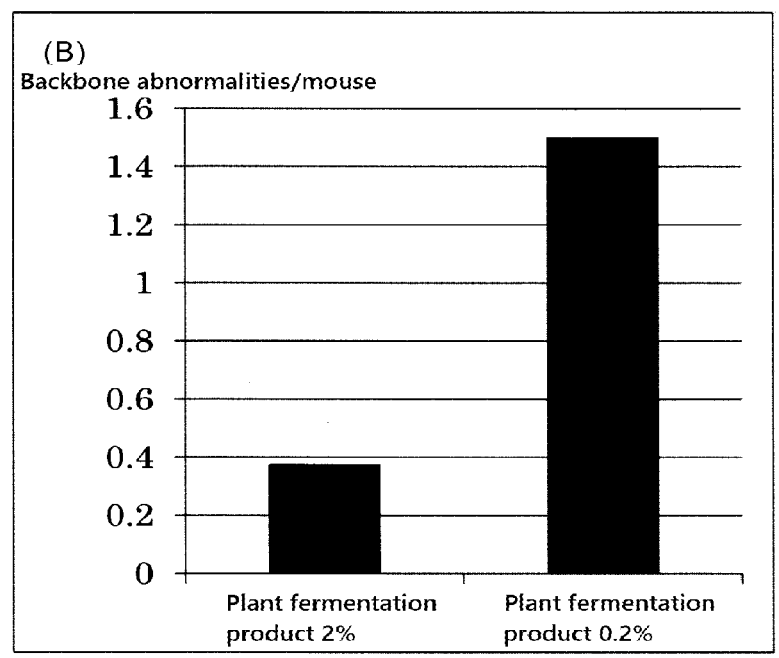
Figure 9:
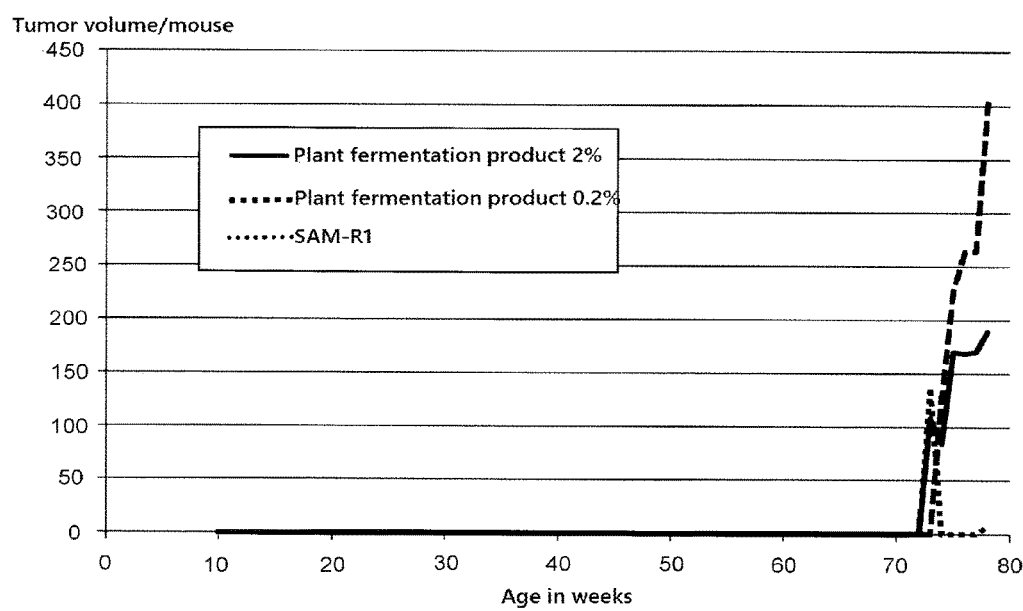
FIG. 9 shows changes in the volume of projections occurring mainly in the groin for normal (SAM-R1) and senescence accelerated (SAM-P1) mice in Test Example 2.

FIG. 4 shows survival curves of mice; and FIG. 5 shows the results of Kaplan-Meyer analysis of the survival rate of mice. Table 1 is a table in which the average days of the survival of three groups of mice receiving the plant fermentation product, CoQ10, and reduced CoQ10 were compared; and Table 2 shows the average and median values of survival periods and the maximum period of growth of mice. FIG. 6 shows changes in the total senescence evaluation score; FIG. 7 shows the results of a significant difference analysis of the total senescence evaluation score for mice at ages of 54 and 60 weeks; and FIG. 8 shows a comparison of backbone curvatures of mice at ages of 54 and 60 weeks. In addition, FIG. 9 shows a comparison of changes in the volume of projection that frequently occurred in a period when mice were kept for a period beyond an age of 60 weeks.

From FIG. 4, it turned out that the survival rate of mice was higher in the group receiving 2% of the plant fermentation product than the group receiving 0.2% of the plant fermentation product and was dependent on concentration. In addition, it was shown that from FIG. 5, a significant difference test between both the groups resulted in a P value=0.00461 being calculated by the Cox-Mantel-Henzel test of significant difference, and the group receiving 2% of the plant fermentation product had a significant longevity-extending effect.

Regarding the average age of weeks (and average number of days) calculated in the Kaplan-Meyer analysis (FIG. 5), a comparison was made with the results of examinations with CoQ10 and reduced CoQ10 using mice of the same species (SAM-P1, male) (Non-Patent Literature 14) (Table 1). The average number of days for the group receiving 2% of the plant fermentation product (624.475 days) seemed to be longer, which was beyond the range of error, relative to those for the groups receiving CoQ10 (517.89 days) and reduced CoQ10 (519.64 days). On the other hand, it has been reported that no significant difference was found between the groups receiving CoQ10 and reduced CoQ10.

TABLE 1

|  | Average value Age in weeks (Days) | CoQ10 Age in weeks (Days) | CoQ10H2 Age in weeks (Days) |
|---|---|---|---|
| Plant fermentation product 2% | 89.250 (624.475) | 73.98 (517.89 ± 82.39) | 74.234 (519.64 ± 79.53) |
| Plant fermentation product 0.2% | 66.000 (462.000) | | |
| Control | | | 77.714 (544.07 ± 64.76) |

TABLE 2

| | Survival period (days) | | |
|---|---|---|---|
| | Average value | Median value | Maximum period of survival |
| Plant fermentation product 2% | 89.250 | 83.000 | 114 |
| Plant fermentation product 0.2% | 66.000 | 62.000 | 96 |

As shown in FIG. 6, the group receiving 2% of the plant fermentation product exhibited a delay of the onset of senescence, compared to the group receiving 0.2% of the plant fermentation product, and had a lower value of the total senescence score throughout the experimental period, relative to the group receiving 0.2% of the plant fermentation product.

As shown in FIG. 6, the group receiving 2% of the plant fermentation product provided a lower total senescence index score at all ages in weeks than the group receiving 0.2% of the plant fermentation product; and the group receiving 2% of the plant fermentation product had a significantly lower senescence score with P<0.05 in a t-test at both ages of 54 and 60 weeks at which a significant difference test was performed, as compared to the group receiving 0.2% of the plant fermentation product (FIG. 7).

At both ages of 54 and 60 weeks, the group receiving 2% of the plant fermentation product exhibited a significantly lower value of the backbone senescence index score than the group receiving 0.2% of the plant fermentation product, showing that the plant fermentation product concentration-dependently inhibits backbone curvature abnormality associated with aging (FIG. 8).

It is known that mice spontaneously develop tumors, of which most are lymphoma, generally beyond an age of 60 weeks. In Test Example 2, at ages of more than 70 weeks, since both normal mice (SAM-R1) and senescence accelerated mice (SAM-P1) developed a projection largely at the groin, its size was determined as an approximate volume defined by minor diameter×major diameter×height to monitor changes in its volume (FIG. 9). The projection was not subjected to cytological diagnosis for carcinoma, and thus was provisionally referred to as a "projection". Changes in the projection size were comparative in the group of senescence accelerated mice receiving 2% of the plant fermentation product and in the group of normal mice; however, the group of senescence accelerated mice receiving 0.2% of the plant fermentation product exhibited a greater change in the projection size than the former groups.

INDUSTRIAL APPLICABILITY

The senescence retarding agent of the present invention has an effect of retarding the onset of senescence symptoms associated with aging of animals and an effect of extending their survival. The senescence retarding agent is the first example that lead to the retardation of senescence symptoms and at the same time, exhibited a dose-dependent and significant increase in the survival rate of oxygen-sensitive nematodes having fundamental requirements for animals, in addition to mammalian animals, and thus can be used as a new medicament or food that not only retards a variety of senescence symptoms, but also prolongs survival.

The invention claimed is:

1. A senescence retarding agent, comprising a plant fermentation product as an active ingredient, the plant fermentation product being a mixture of the following:
   (a) a koji mold-fermented product of barley, black soybean, red rice, black rice, adzuki bean, adlay, Japanese millet, foxtail millet, and millet;
   (b) a yeast-and/or lactic acid bacterium-fermented product of mikan (mandarin orange), grape, apple, yamabudo (crimson glory grape), peach, kaki (Japanese persimmon), *papaya*, nashi (Japanese pear), watermelon, ume (Japanese apricot), fig, karin (Chinese quince), pumpkin, kumquat, yuzu (Chinese lemon), loquat, apricot, jujube, chestnut, matatabi (silvervine), and sumomo (Japanese plum);

(c) a yeast-and/or lactic acid bacterium-fermented product of murasaki-imo (purple sweet potato), kikuimo (Jerusalem artichoke), carrot, onion, satsuma-imo (sweet potato), satoimo (taro), jinenzyo (Japanese yam), daikon (Japanese radish), akakabu (red turnip), gobo (burdock root), renkon (lotus root), yacon, yuri-ne (lily bulb), kuwai (arrowhead), ginger, garlic, and turmeric;

(d) a yeast-and/or lactic acid bacterium-fermented product of cabbage, shiso (perilla), mulberry leaves, dokudami (Korean houttuynia), yomogi (wormwood), kumazasa (kuma bamboo grass), and dandelion;

(e) a yeast-and/or lactic acid bacterium-fermented product of kombu (sea tangle), wakame (*Undaria pinnatifida*), and mozuku (*Nemacystus decipiens*);

(f) a yeast-and/or lactic acid bacterium-fermented product of black sesame seeds, walnuts, and ginkgo nuts; and (g) a yeast-and/or lactic acid bacterium-fermented product of maitake (*Grifola frondosa*) and shiitake (*Lentinus edodes*).

2. The senescence retarding agent according to claim 1, wherein the plant fermentation product comprises the following amino acids in amounts per 100 g of the plant fermentation product:

| | |
|---|---|
| Arginine | 0.2 to 0.6 g |
| Lysine | 0.1 to 0.7 g |
| Histidine | 0.1 to 0.4 g |
| Phenylalanine | 0.2 to 0.8 g |
| Tyrosine | 0.1 to 0.6 g |
| Leucine | 0.3 to 1.2 g |
| Isoleucine | 0.2 to 0.8 g |
| Methionine | 0.05 to 0.30 g |
| Valine | 0.2 to 0.9 g |
| Alanine | 0.2 to 0.9 g |
| Glycine | 0.2 to 0.7 g |
| Proline | 0.4 to 1.2 g |
| Glutamic acid | 1.2 to 3.0 g |
| Serine | 0.2 to 0.8 g |
| Threonine | 0.2 to 0.7 g |
| Aspartic acid | 0.4 to 1.5 g |
| Tryptophan | 0.03 to 0.15 g |
| Cystine | 0.05 to 0.40 g. |

3. The senescence retarding agent according to claim 1, wherein the plant fermentation product comprises the following organic acids in amounts per 100 g of the plant fermentation product:

| | |
|---|---|
| Citric acid | 0.5 to 1.2 g |
| Malic acid | 0.05 to 0.5 g |
| Succinic acid | 0.04 to 0.3 g |
| Lactic acid | 0.5 to 6.0 g |
| Formic acid | 0.01 to 0.1 g |
| Pyruvic acid | 0.005 to 0.05 g |
| Free γ-aminobutyric acid | 0.01 to 0.05 g. |

4. The senescence retarding agent according to claim 1, wherein the plant fermentation product comprises the following polyphenols in amounts per 1 g of the plant fermentation product:

| | |
|---|---|
| Caffeic acid | 20 to 50 µg |
| o-aminobenzoic acid | 10 to 25 µg |

-continued

| | |
|---|---|
| Ferulic acid | 40 to 70 µg |
| p-Coumaric acid | 15 to 40 µg |
| Daizein | 40 to 65 µg |
| Genistein | 65 to 90 µg |
| Glycitein | 2 to 8 µg |
| Quercetin | 3 to 12 µg |
| Hesperetin | 200 to 300 µg |
| Naringenin | 30 to 60 µg. |

5. The senescence retarding agent according to claim 1, comprising at least one lactic acid bacterium selected from the group consisting of *Pediococcus acidilacti* (*P. acidilacti*), *Lactobacillus brevis* (*L. brevis*), *Leuconostoc mesenteroides* (*L. mesenteroides*), *Lactobacillus plantarum* (*L. plantarum*), *Lactococcus lactis*(*L. lactis*), *Lactobacillus sakei* (*L. sakei*), *Pediococcus pentosaceus* (*P. pentosaceus*), *Lactobacillus casei* (*L. casei*), and *Lactobacillus curvatus* (*L. curvatus*).

6. The senescence retarding agent according to claim 1, comprising at least one yeast selected from the group consisting of *Saccharomyces cerevisiae*(*S. cerevisiae*) and *Zygosaccharomyces rouxii* (*Z. rouxii*).

7. A food or drink comprising the senescence retarding agent according to claim 1.

8. The senescence retarding agent according to claim 1, which is a medicament.

9. A longevity extending agent, comprising a plant fermentation product as an active ingredient, the plant fermentation product being a mixture of the following:

(a) a koji mold-fermented product of barley, black soybean, red rice, black rice, adzuki bean, adlay, Japanese millet, foxtail millet, and millet;

(b) a yeast-and/or lactic acid bacterium-fermented product of mikan (mandarin orange), grape, apple, yamabudo (crimson glory grape), peach, kaki (Japanese persimmon), *papaya*, nashi (Japanese pear), watermelon, ume (Japanese apricot), fig, karin (Chinese quince), pumpkin, kumquat, yuzu (Chinese lemon), loquat, apricot, jujube, chestnut, matatabi (silvervine), and sumomo (Japanese plum);

(c) a yeast-and/or lactic acid bacterium-fermented product of murasaki-imo (purple sweet potato), kikuimo (Jerusalem artichoke), carrot, onion, satsuma-imo (sweet potato), satoimo (taro), jinenzyo (Japanese yarn), daikon (Japanese radish), akakabu (red turnip), gobo (burdock root), renkon (lotus root), yacon, yuri-ne (lily bulb), kuwai (arrowhead), ginger, garlic, and numeric;

(d) a yeast-and/or lactic acid bacterium-fermented product of cabbage, shiso (perilla), mulberry leaves, dokudami (Korean houttuynia), yomogi (wormwood), kumazasa (kuma bamboo grass), and dandelion;

(e) a yeast-and/or lactic acid bacterium-fermented product of kombu (sea tangle), wakame (*Undaria pinnatifida*), and mozuku (*Nemacystus decipiens*);

(f) a yeast-and/or lactic acid bacterium-fermented product of black sesame seeds, walnuts, and ginkgo nuts; and (g) a yeast-and/or lactic acid bacterium-fermented product of maitake (*Grifola frondosa*) and shiitake (*Lentinus edodes*).

* * * * *